United States Patent [19]
Sindrey et al.

[11] Patent Number: 5,290,920
[45] Date of Patent: Mar. 1, 1994

[54] METHOD OF PURIFYING HUMAN EPIDERMAL GROWTH FACTOR

[75] Inventors: Dennis R. Sindrey, Etobicoke; Chandra M. Dwivedi, Mississauga, both of Canada

[73] Assignee: Allelix Biopharmaceuticals Inc., Ontario, Canada

[21] Appl. No.: 869,176

[22] Filed: Apr. 16, 1992

[51] Int. Cl.$^5$ ............ C07K 3/00; C07K 13/00
[52] U.S. Cl. ............ 530/412; 530/415; 530/416; 530/417; 530/324; 530/399; 930/120
[58] Field of Search ............ 530/324, 399, 412, 415, 530/416, 417; 514/12

[56] References Cited

U.S. PATENT DOCUMENTS 4,717,717  1/1988  Finkenaur ............ 514/21

FOREIGN PATENT DOCUMENTS 205051   3/1986   European Pat. Off.
240031   3/1987   European Pat. Off.
357391   3/1989   European Pat. Off.
352839   7/1989   European Pat. Off.
91/15228 10/1991  PCT Int'l Appl.

OTHER PUBLICATIONS

Nishimura et al, "Heterogeneity Of Human Epidermal Growth Factor/Urogastrone From Human Urine," Chem. Pharm. Bull., 33(9):4037–4040, (1985).

O'Hare et al, "The Optimization Of RP-HPLC Of Proteins With Large Pore-Size Short Alkyl-chain-Bonded Silica (Ultrapore RPSC) And Its Application To Epidermal Growth Factor," Protides Biological Fluids, 30:723–726.

Gordon et al, "Capillary Electrophoresis," Science, 242:224–228, (1988).

Haigler et al, "Visualization By Fluorescene Of The Binding And Internalization Of Epidermal Growth Factor In Human Carcinoma Cells A-431," Proc. Natl. Acad. Sci. USA 1, 75:3317-3321, (1978).

Hancock, "CRC Handbook Of HPLC For The Separation Of Amino Acids, Pepties, And Proteins," CRC Press, Inc., vol. 1 Table of contents only.

Sofer et al, "Designing An Optimal Chromatographic Purification Scheme For Proteins," Biotechniques, pp. 198–203, (1983).

Burgoyne et al, "High Performance Preparative Scale Purification Of Human epidermal Growth Factor," Analusis, 15(8):48–53 (1987).

Okumura et al, "Improvement In Wound Healing By Epidermal Growth Factor (EGF) Ointment. I. Effect of Nafamostat, Gabexate, Or Gelatin On Stabilization And Efficay Of EGF", Pharmaceutical Research, 7:1289–1293, 1990.

Primary Examiner—F. T. Moezie
Attorney, Agent, or Firm—Foley & Lardner

[57] ABSTRACT

Human epidermal growth factor is provided in an ultrapure form characterized by the absence of protein contaminants detectable by capillary electrophoresis analysis. A method for obtaining such ultrapure human epidermal growth factor includes fractionation of a human epidermal growth factor preparation by reversed phase high performance liquid chromatography in the presence of a cationic ion-pairing agent.

12 Claims, 3 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Asn Ser Asp Ser Glu Cys Pro Leu Ser His Asp Gly Tyr Cys Leu His
 1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
            35                  40                  45

Trp Trp Glu Leu Arg
 50
```

METHOD OF PURIFYING HUMAN EPIDERMAL GROWTH FACTOR

Epidermal growth factor, or EGF, is a protein produced naturally by many species of mammals, including humans. It stimulates the growth of new skin and other epithelial tissues, and thus has great potential as a wound healing agent. Of particular clinical interest are its regenerative effects on ophthalmic wounds created for example during corneal transplant surgery, on wounds of the skin, for example burns and grafts, and on stomach and other ulcers.

The human form of epidermal growth factor consists of 53 amino acids arranged in the specific sequence (SEQ. ID NO:1) illustrated below:

Asn—Ser—Asp—Ser—Glu—Cys—Pro—Leu—Ser—His—
Asp—Gly—Tyr—Cys—Leu—His—Asp—Gly—Val—Cys—
Met—Tyr—Ile—Glu—Ala—Leu—Asp—Lys—Tyr—Ala—
Cys—Asn—Cys—Val—Val—Gly—Tyr—Ile—Gly—Glu—
Arg—Cys—Gln—Tyr—Arg—Asp—Leu—Lys—Trp—Trp—
Glu—Leu—Arg$_{53}$

The active protein incorporates three disulfide bridges and is free from posttranslational modifications such as glycosylation, acetylation and the like.

Human EGF has been obtained from a variety of sources including human fluids, such as urine. More recently, recombinant DNA-based techniques have been successfully applied, and can now provide human epidermal growth factor (hEGF) in the amounts required for clinical and commercial purposes. As an alternative to these methods, automated techniques of protein synthesis, in which component amino acids are coupled chemically and in correct sequence, can also be applied to produce EGF. As a prelude to using hEGF as a pharmaceutical product however, it is necessary for many reasons to provide the protein in essentially pure form. For instance, the use in clinical trials of hEGF that is essentially pure will permit observed effects to be attributed solely to EGF and not to some structurally related contaminant. Also, obtaining EGF in essentially pure form will provide for high specific activity i.e. highest potency per unit amount of EGF, and permit administration of the smallest possible dosage size to treat a given indication. Furthermore, removal of contaminants will effectively reduce the possibility of side effects, which is especially important when EGF is administered to treat chronic ailments such as persistent ulcers.

One method currently used to purify proteins, and to analyze protein purity, is reversed phase high performance liquid chromatography (RP-HPLC). Like other HPLC techniques, the reversed phase approach exploits variability in the rates at which specific proteins migrate through a bed of silica microspheres. In the reversed phase HPLC technique, however, alkylated silica micropheres are used, and migrating proteins are subjected to a two phase solvent system which exploits protein charge and accents separation. Most typically, the solvent system consists of a water phase and an organic phase typically containing acetonitrile and an ion-pairing agent (also known as a charge modifier) such as trifluoroacetic acid (TFA), the relative proportions of which are altered gradiently by automated blending as the protein sample migrates through the column. When analyzed by this technique, a protein preparation which elicits but a single detectable protein species (measured by UV absorbance either at 214 nm or at 280 nm) is deemed to consist of one protein species, and is thus characterized as an essentially pure protein. Proteins exhibiting this degree of purity are sometimes characterized as being of "HPLC-grade".

The reversed phase HPLC technique has been used to purify and to assess the purity of human EGF obtained from various sources. In Chem. Pharm. Bull., 1985, 33(9):4037, Nishimuro et al describe the isolation and analysis of EGF from human urine. The authors employed the reversed phase HPLC method, using the anionic TFA as ion-pairing agent and an acetonitrile/water solvent system, to identify as many as ten subspecies of human EGF in a substantially purified EGF preparation. O'Hare et al describe application of reversed phase HPLC to purification of EGF and, in combination with a select type of column packing, employed the conventional water/acetonitrile solvent system supplemented with one of the anionic ion-pairing agents, TFA and heptafluorobutyric acid (HFBA). In WO91/15228, Parikh describes a method for purifying recombinant human EGF employing, in an intermediate step of the process, a reversed phase HPLC approach that also employs the conventional water/acetonitrile/TFA solvent system.

It has now been determined, however, that EGF compositions exhibiting HPLC-grade purity measured by conventional means in fact contain protein impurities detectable by the more sensitive analytical technique of capillary electrophoresis (CE). It is accordingly an object of the present invention to provide human EGF in a form that is essentially free from protein contaminants detectable by capillary electrophoresis. It is another object of the present invention to provide a method for obtaining human EGF in essentially pure form. It is a further object of the present invention to provide a pharmaceutical composition which contains essentially pure human EGF.

SUMMARY OF THE INVENTION

The present invention provides human EGF in essentially pure form, i.e., in a form that is essentially free from protein contaminants, as determined by capillary electrophoresis analysis. The capillary electrophoresis technique offers a more sensitive measure of EGF purity, as demonstrated herein by its ability to detect impurities in human EGF preparations determined to be pure by conventionally applied HPLC analysis.

In one aspect of the present invention, there is provided a composition which consists of pure human EGF and is essentially free from protein contaminants detectable by capillary electrophoresis. In one specific embodiment of this aspect of the present invention, the essentially pure human EGF is provided in lyophilized form.

According to another aspect of the present invention, there is provided a process for preparing a pharmaceutical composition, which comprises the step of combining the pure human EGF with a pharmaceutically acceptable carrier. In a related aspect of the present invention, there is provided a pharmaceutical composition comprising the pure human EGF and a pharmaceutically acceptable carrier.

In a further aspect of the present invention, there is provided a method for purifying human EGF, which comprises the step of fractionating a human EGF preparation by reversed phase HPLC in the presence of a cationic ion-pairing agent, to separate human EGF from protein contaminants resident in the preparation, and then collecting essentially pure human EGF. In one embodiment of the invention, the EGF preparation is first obtained by fractionation of an EGF solution on anion exchange chromatography.

In another aspect of the present invention, there is provided a method of obtaining pure human EGF, which comprises the steps of subjecting a human EGF preparation to anion exchange chromatography, collecting the EGF-containing eluant, subjecting the eluant to reversed phase HPLC in the presence of a cationic ion-pairing agent, and then collecting essentially pure human EGF. According to one embodiment of the invention, the essentially pure human EGF so collected is then subjected to a desalting step.

These and other aspects of the present invention are now described in greater detail, with reference to the accompanying drawings, in which:

BRIEF REFERENCE TO THE DRAWINGS

DETAILED DESCRIPTION OF THE INVENTION AND ITS PREFERRED EMBODIMENTS

Figure 1:
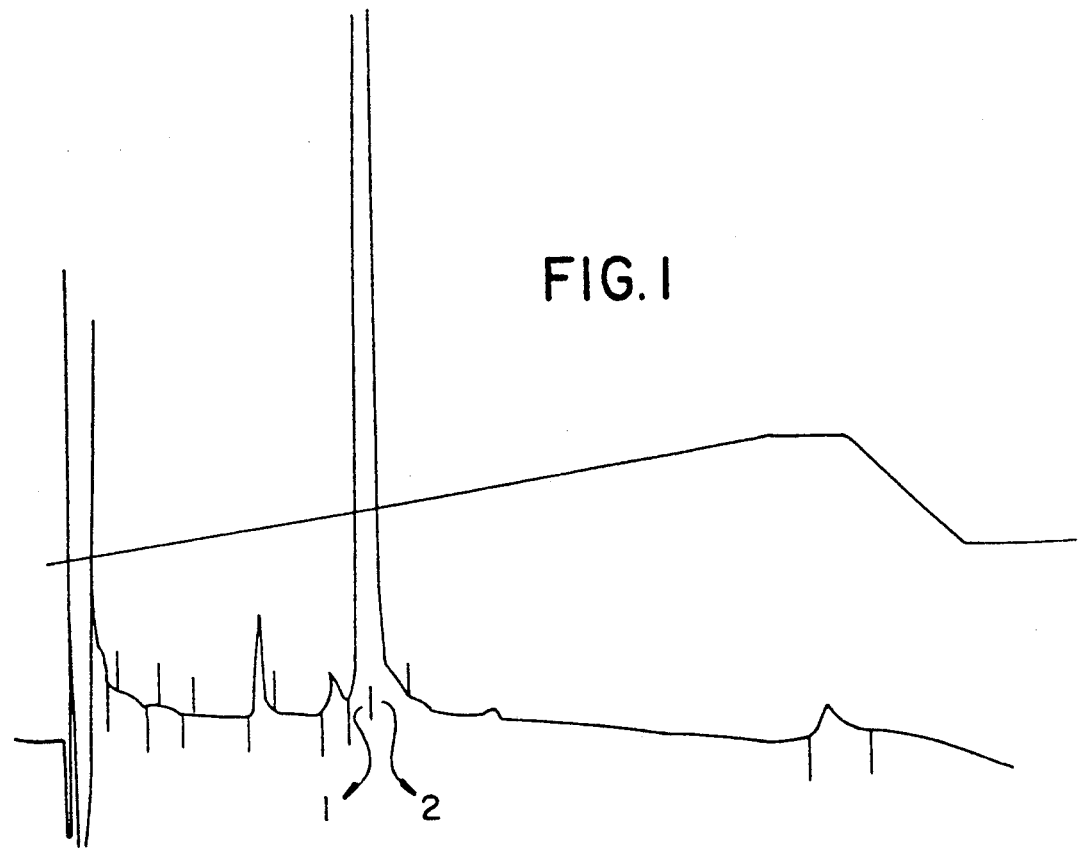
FIG. 1 illustrates the absorbance ($A_{214}$) profile of a substantially pure EGF sample analyzed by conventional RP-HPLC techniques.

The invention relates to human EGF in a form that is essentially free from protein contaminants detectable by capillary electrophoresis (CE). For brevity, EGF exhibiting this purity is sometimes herein referred to as "CE-grade" human EGF, or as "essentially pure" human EGF.

For the purposes of the present specification, the terms "hEGF", "human EGF" and "human epidermal growth factor " are used interchangably with reference to a non-glycosylated protein consisting essentially of 53 L-amino acid residues arranged by amide linkage in the sequence (SEQ.ID No. 1) identified below:

Asn—Ser—Asp—Ser—Glu—Cys—Pro—Leu—Ser—His—
Asp—Gly—Tyr—Cys—Leu—His—Asp—Gly—Val—Cys—
Met—Tyr—Ile—Glu—Ala—Leu—Asp—Lys—Tyr—Ala—
Cys—Asn—Cys—Val—Val—Gly—Tyr—Ile—Gly—Glu—
Arg—Cys—Gln—Tyr—Arg—Asp—Leu—Lys—Trp—Trp—
Glu—Leu—Arg$_{53}$

Those skilled in the art of protein chemistry will appreciate that slight variations in human EGF structure may occur, depending to a great extent on the nature of the EGF source. Cellularly-produced human EGF, i.e. hEGF derived either from urine or from microbial sources, may contain a small proportion of C-terminally amidated protein or C-terminally truncated protein, or oxidized protein, for example. On the other hand, synthetically-derived human EGF may contain a small proportion of EGF molecules that are oxidized or incorporate amino acids bearing modified alpha carbon side chains. The CE-grade human EGF of the present invention may contain EGF molecules having such modifications, provided of course that they are present in amounts small enough as to be undetectable by capillary electrophoresis analysis.

The CE-grade human EGF of the present invention can be characterized, more particularly, by migration as a single absorbance peak at 214 nm when subjected to analysis by capillary electrophoresis. The capillary electrophoresis technique separates proteins on the basis of mass/charge ratio within a capillary having a bore of miniscule diameter, as reviewed generally by Gordon et al in Science, 1988, 242:224. Briefly, aqueous samples of the protein preparation to be analyzed are drawn by vacuum into the capillary and subjected to an electric field, with subsequent migration of protein species through the capillary being monitored by detecting absorbance desirably at 214 nm. In the specific case of human EGF, resolution of protein species is suitably achieved using EGF preparations containing from about 0.2 mg/ml to about 1.0 mg/ml in an aqueous vehicle buffered, for instance by phosphate, to about pH2. The rate at which sample is loaded into the capillary is uniform, through it is desirable to load sample for from 2 to 10 seconds depending on initial purity of the sample, so that contaminants, if present, are loaded in detactable amounts. A 5–10 ng load of the EGF sample will generally be sufficient to identify protein contaminants in the CE-based absorbance profile.

In addition to exhibiting CE-grade purity, the essentially pure human EGF of the present invention is characterized by a remarkably good bioactivity, as determined by mitogenicity assay, described for example by Aitken et al, Cancer Res., 1980, 43:4681, incorporated herein by reference. This in vitro bioassay measures quantitatively the extent to which a given EGF concentration stimulates cell as division as demonstrated by the incorporation of 3H-thymidine into DNA. The CE-grade human EGF of the present invention elicits, in this assay, an activity at least equivalent to EGF standards.

The CE-grade human EGF is also characterized by a molecular weight that is virtually equivalent to its theoretical molecular weight of 6217 daltons, as determined by ion spray mass spectrometric analysis.

Human EGF having the characteristics just described can be obtained by subjecting a human EGF preparation, preferably a substantially purified human EFG preparation, to reversed phase high performance liquid chromatography (RP-HPLC) in the presence of a cationic ion-pairing agent. Those skilled in the art will appreciate that ion-pairing agents employed conventionally to achieve EGF separation by RP-HPLC include such anionic modifiers as heptafluorobutyric acid (HFBA) and, more commonly, trifluoroacetic acid (TFA). As is demonstrated herein, however, these anionic ion-pairing agents, and particularly TFA, do not provide the resolution required to separate human EGF from structurally-related and other protein contaminants. According to the present invention, it has been found that cationic ion-pairing agents, especially amine-based ion-pairing agents (known also as "charge modifiers") possess the charge characteristics best suited for resolution of EGF, and thus for separating human EGF from protein contaminants.

One aspect of the present invention thus resides in a method for obtaining essentially pure human EGF, which comprises the step of subjecting a human EGF preparation to fractionation by reversed phase high performance liquid chromatography in the presence of a cationic ion-pairing agent. Essentially pure EGF is then recovered by collecting selectively the main protein peak migrating through the column (as determined by absorbance at 280 nm or more preferably at 214 nm), to the exclusion of contaminants represented in the neighbouring smaller protein peaks.

Among the cationic ion-pairing agents that can be used are the amine-based agents including di- and tri-lower alkyl amines such as trimethylamine, triethylamine, tributylamine and dipropylamine. Especially preferred as the ion-pairing agent is triethylamine. The ion-pairing agent may be used in salt form, and triethylamine phosphate, prepared by mixing triethylamine and phosphoric acid, is preferred in this regard. Further, the ion-pairing agent optionally in salt form may be formulated in an alkanol solvent, such as methanol, propanol or isopropanol, if desired, or in organic acid such as formic acid.

When salts of the amine-based ion-pairing agent are used, it is desirable, as a final step in the EGF purification process, to remove the ion-pairing agent by desalting the material collected from the reversed phase HPLC column. Desalting can be performed by subjecting the collected sample to any one of a variety of suitable desalting methods, such as by gel filtration, ultrafiltration, or reversed phase HPLC in which a volatile ion-paring agent is employed, such as the conventional ion-paring agents trifluoroacetic acid (TFA) and heptafluoroacetic acid (HFBA).

The cationic, e.g. amine-based, ion-pairing agent is incorporated, and the RPHPLC purification process is performed, in the manner conventional when other ion-pairing agents are used. The two solvent solutions to be blended gradiently during the HPLC run are first prepared, to provide a "solvent A" solution containing water and the amine-based ion-pairing agent, and a "solvent B" solution that comprises water, the amine-based ion-pairing agent, and about 80% of an organic component such as acetonitrile, methanol or 1-propanol. Best results are obtained using acetonitrile. Each solvent is prepared by mixing commercially available HPLC-grade reagents and then filtering, for example through a 0.45 micron filter, followed by degassing to remove oxygen, all according to conventional protocols.

When triethylamine phosphate (TEAP) is used as the ion-pairing agent, solvent concentrations of TEAP in the range from 0.05 to 1.0% by volume may be used, with best separations being achieved at around 0.4% TEAP by volume. In a particularly preferred embodiment of the present invention, therefore, EGF purification is achieved by reversed phase HPLC using as solvent solutions a solvent A which consists of water to which has been added 0.4% triethylamine and 0.4% phosphoric acid (85%), and a solvent B which consists of water and 80% acetonitrile to which has been added 0.4% triethylamine and an amount of phosphoric acid (85%), generally about 0.4%, sufficient to render the pH equivalent to that in solvent A.

Apart from incorporation of the amine-based modifier in the solvents, fractionation of human EGF preparations can be achieved using HPLC devices that are available commercially, in the manner conventional for reversed phase HPLC techniques (see for example CRC Handbook of HPLC for the Separation of Amino Acids, Peptides and Proteins, Volume 1, 1984, CRC Press Inc.). Columns within which the fractionation occurs may be packed for example with silica beads bearing alkyl groups of a uniform length in the range from C4 to C18, with C18 being particularly suitable for EGF separation. It has been found that columns packed with C-18 beads having a uniform size of about 10 microns and a pore size of about 120 Angstroms are well suited for EGF purification. Such columns are available commercially, as cartridges for incorporation into HPLC machines, from Waters and are sold under the trade name "Microbondapak". In a preferred embodiment, the HPLC column is packed with C-18 beads having a uniform particle size of about 5 microns and a pore size of about 300 Angstroms. Such columns are available commercially, from Rainin Instrument Co., Inc., Woburn, Mass. and are sold under the trade name "Dynamax".

Fractionation of human EGF preparations is achieved by loading a sample of the preparation into the HPLC device, and then adjusting the relative blend of solvents A and B, as desired. While it is possible to generate a linear gradient from 100% solvent A through to 100% solvent B, a gradient that is more desirable for EGF fractionation has been found to consist of a gradient that proceeds from 70%A/30%B through 40%A/60%B and returning to 70%A/30%B. This gradient is ideally established using a flow rate of about 1 ml of EGF solution, desirably a saturated EGF solution, per minute of loading. Under these conditions, essentially pure EGF elutes at about 15 minutes, and in about 30% acetontrile.

The advantage of using triethylamine as the ion-pairing agent is evident when, as is conventional, migration of protein through the HPLC column is monitored by absorbance at 214 nm. As is shown in the Figures herein, contaminants in the injected EGF sample are resolved separately from EGF which migrates as a single large absorbance peak. This enables the essentially pure EGF to be collected as a distinct fraction of eluant, to the exclusion of other material which separates therefrom during column migration. The essentially pure EGF eluted from the reversed phase HPLC column may be lyophilized in the conventional manner, preferably immediately after collection to avoid oxidation of the EGF, and stored over long periods at a temperature for instance of about −70° C.

The CE-grade human EGF may be formulated for its various known therapeutic use. Such formulations may be of a type already established for EGF administration, such as gels, solutions, suspensions or dispersions optionally stabilized with a water soluble cellulose derivative in the manner detailed in U.S. Pat. No. 4,717,717. Creams, lotions and ointments comprising essentially pure EGF may be applied topically to promote wound healing. Cream formulations suitably comprise surface active agents such as derivatized fatty acids or sorbitol, an oil based carrier composed of petroleum jelly, paraffin or the like, water and such other excipients as are used routinely in the art to formulate protein drugs. Reference may be made to EP 205,051, incorporated herein by reference, for guidance in formulating EGF creams. When combined with an ophthalmologically compatible carrier, EGF will be useful to promote healing of corneal damage. Solutions of EGF may, for example, be applied as eye drops. Corneal mortar compositions may also be employed, as detailed in EP 240,031.

The EGF formulations may also be supplemented with an amount of a second therapeutic agent, if desired. For example, wound healing combinations of EGF and one or more of fibroblast growth factor, a non-steroidal anti-inflammatory agent, an anti-bacterial agent and the like may be employed therapeutically.

It will be appreciated that use of EGF in essentially pure form and in a pharmaceutical context offers the distinct advantages of reducing side effects and immunogenicity that may be elicited by contaminants residing in compositions having otherwise lower levels of purity, and of reducing the amount of EGF required to elicit a given physiological response.

It will also be understood that the technique herein described for purifying EGF can be applied to EGF compositions obtained by various techniques, including extraction from human urine, from microbial sources of EGF and from synthetic sources. Generally, EGF isolated from such sources is desirably obtained in substantially purified form i.e. subjected to at least one column fractionation step, before being subjected to the reversed phase HPLC process of the present invention. A preparation consisting of substantially purified human EGF is characterized, in general, by a purity of at least about 80%, and more desirably exhibits a purity as measured by the capillary electrophoresis technique that is at least about 90-95% pure. When obtained from a microbial source such as bacteria for example, the microbial extracts are desirably first treated to concentrate the EGF such as by diafiltration, and the treated samples are then subjected to any of the various fractionation techniques useful for EGF enrichment. For example, the crude EGF sample may be subjected to reversed phase chromatography on CG71 and/or to anion exchange chromatography e.g. using a Q-Sepharose column, a DEAE-Sepharose column or an S-Sepharose column.

The extent to which the crude sample is enriched for EGF prior to reversed phase HPLC-based purification will depend to a large extent on the environment in which EGF is produced. In this regard, and in accordance with a preferred embodiment of the invention, the EGF source is desirably an *E. coli* transformant that has been engineered genetically to produce EGF as a secreted (periplasmic) or as an excreted (extracelluar) product. In a particularly preferred embodiment of the invention, the EGF source is an *E. coli* transformant which produces EGF as an extracellular product, as described for example by Wong et al in EP 357,391 which is incorporated herein by reference and summarized briefly, infra.

EXAMPLES

For purification according to the protocols specified in the examples hereinbelow, a partially purified preparation of human EGF was first obtained. In particular, human EGF was produced using the bacterial system described by Wong and Sutherland in European patent application 357,391 published Mar. 7, 1990, which is incorporated herein by reference. Briefly, this production system exploits as production host an *E. coli* JM101 strain that uses the tac promoter to drive expression of an EGF precursor bearing the ompA signal peptide, and that excretes mature human EGF to the medium in which the strain is cultured. Prior to RP-HPLC fractionation, a substantially pure preparation of this "excreted" EGF was obtained in the following manner: whole broth obtained from a 10 liter fermentation was separated from cellular biomass by centrifugation (~8500 g for 30 minutes) and then filtered over a 0.3μ membrane. The filtrate was then diafiltered twice in about 2 L of Tris buffer (pH 8.0) using an Amicon 3K cartridge to enhance EGF extraction. The retentate was then fractionated on a CG71 (50–100μ) reversed phase column (200 ml volume, 5 cm bore, Toso-Haas, U.S.A.) equilibrated with 20 mM Tris, 5 mM EDTA at pH 8.0, using a flow rate of about 18 ml/min and using 40% acetonitrile as elution buffer. Eluate from the CG71 column was then loaded onto an anion exchange column, Q-Sepharose-FastFlow (200 ml volume, 5 cm bore, Pharmacia) equilibrated with 20 mM Tris at pH 8.0, and eluted using a flow rate of 8 ml/min and gradiently blended solutions of buffer A (same as equilibration buffer) and of buffer B which consisted of 20 mM Tris, 0.5M NaCl, pH 8.0. Elution was monitored at $A_{280}$ in a reversed phase HPLC assay and fractions identified as containing EGF by comparison with an EGF standard were collected and pooled.

A preparation consisting of the pooled Q-Sepharose fractions was then analyzed by RP-HPLC in C-18 silica using TFA as ion-pairing agent. In particular, the preparation was loaded into a Water's Microbondapak $C_{18}$ column at a rate of 1 ml/minute, and using as buffers 100% water and 0.1% TFA (solvent A), and 80% acetonitrile with 0.1% TFA (solvent B). Eluant was monitored at $A_{214}$. The absorbance profile of the EGF preparation so analyzed is presented in FIG. 1, which reveals numerous protein contaminants among a large single peak containing human EGF, and an estimated EGF purity of about 85%.

Figure 2:
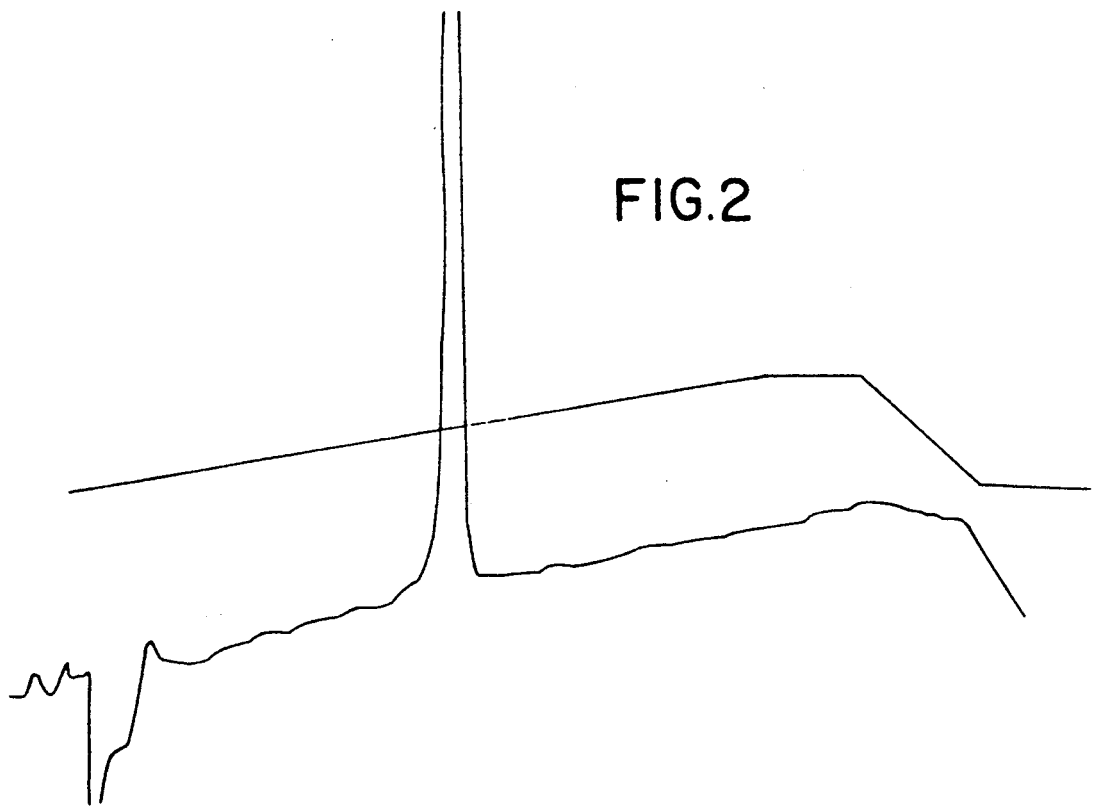
FIG. 2 illustrates the absorbance ($A_{214}$) profile of an EGF sample that is purified from the sample shown in FIG. 1 by conventional RP-HPLC techniques.

For further purification, eluted material representing the main absorbance peak was collected in two fractions, as shown in FIG. 1, and each fraction was then subjected individually to fractionation by reversed phase HPLC using 0.1TFA as ion pairing agent in the conventional manner, and otherwise as just stated for the analytical procedure. As FIG. 2 illustrates, HPLC analysis reveals a single absorbance peak for the material collected as fraction #2 (similar results were obtained with fraction #1), suggesting that human EGF had been obtained in essentially pure i.e. HPLC-grade, form.

EXAMPLE 1

Further analysis of HPLC-grade human EGF

With conventional reversed phase HPLC analysis suggesting that the sample obtained as described above represented pure human EGF, the sample was again analyzed by RP-HPLC, but using a cationic ion pairing agent in place of the conventional anionic ion-pairing agent, TFA.

More particularly, 100 μl of material collected as fraction #2 (FIG. 2) was injected into the HPLC device (Waters HPLC 820 computerized system having two 510 gradient pumps, Waters Wisp autoinjector and Hewlett Packard 1040 scanning diode array detector). Incorporated in the device was a column packed with 5u C-18 silica beads sold under the trade name Dynamax by Rainin (4.1×25 cm, 300 A pore size). Solvents A and B consisted of 100% water supplemented by volume with 0.4% triethylamine and 0.4% phosphoric acid (A), and 80% acetonitrile supplemented with 0.4% triethylamine and 0.4% phosphoric acid. The automated flow rate was 1 ml/min and the solvents were blended using a programmed gradient curve, as follows over the indicated time course (minutes):

| time | % A | % B |
|------|-----|-----|
| 0    | 70  | 30  |
| 1    | 70  | 30  |
| 30   | 30  | 70  |
| 32   | 30  | 70  |
| 37   | 70  | 30  |
| 40   | 70  | 30  |

Figure 3A:
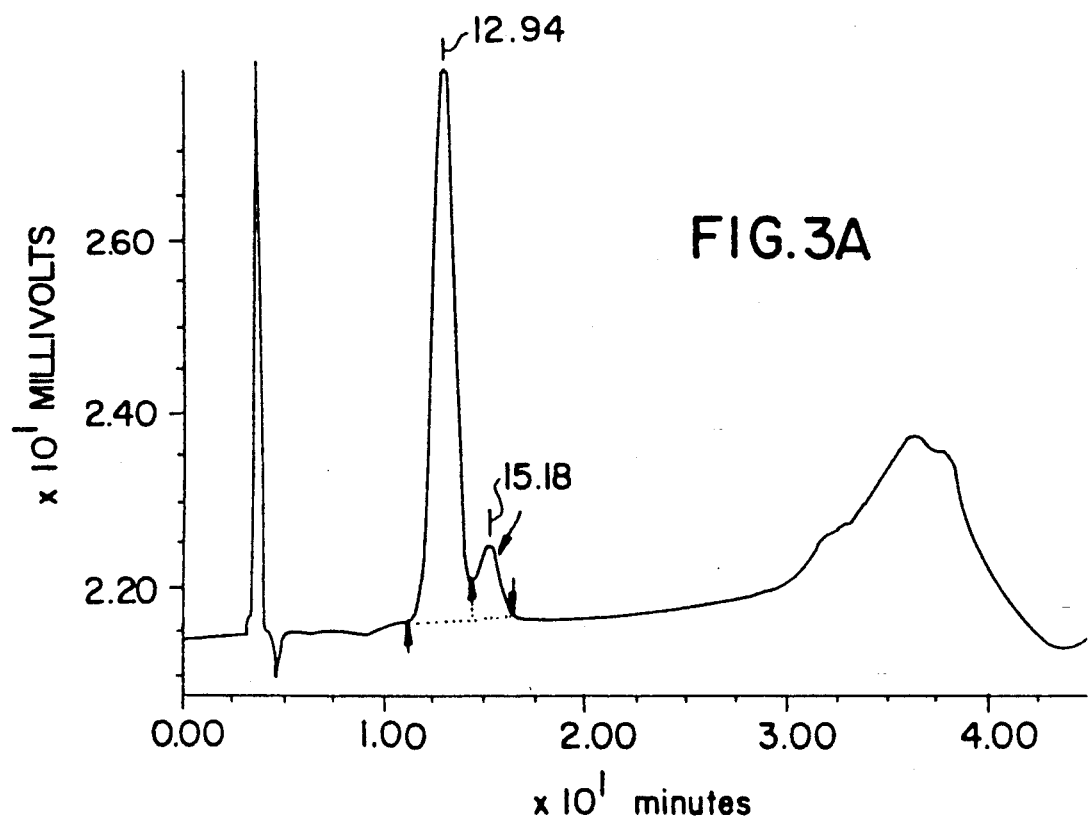
FIG. 3 illustrates the absorbance ($A_{214}$) profile of the EGF sample shown in FIG. 1, but analyzed (FIG. 3A) and purified (FIG. 3B) by the technique of the present invention.
Figure 3B:
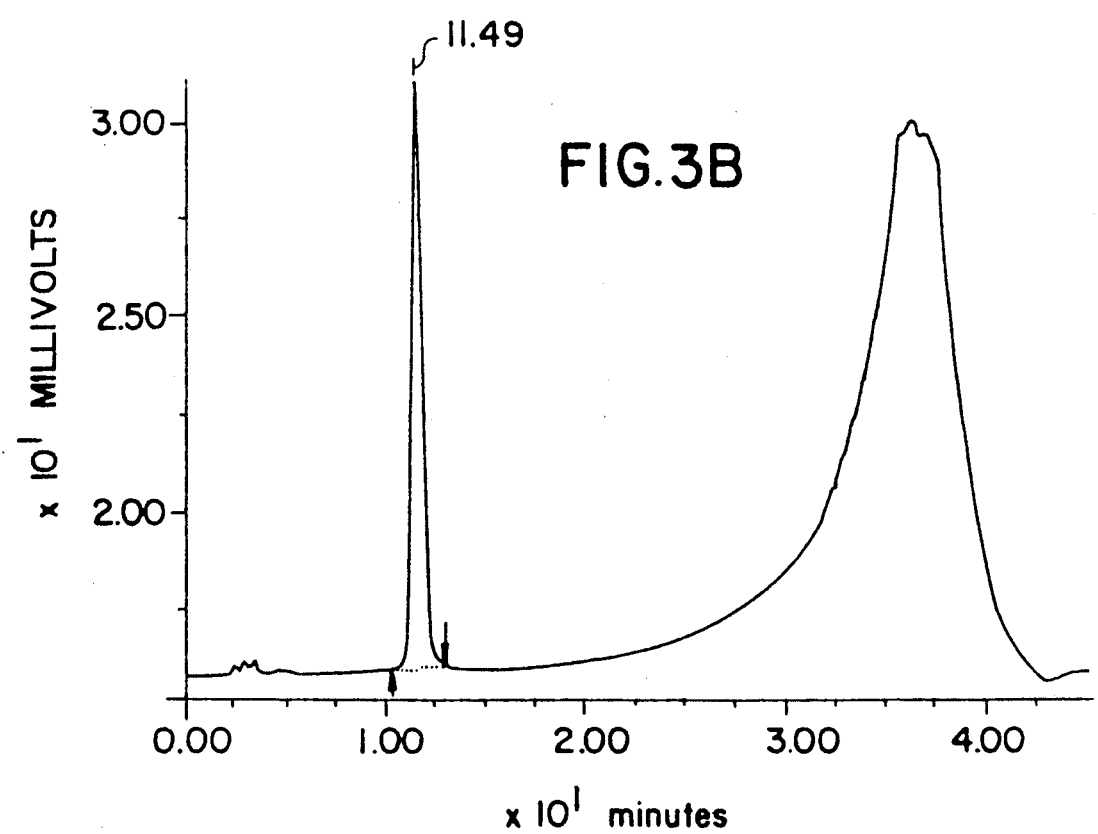

Results of the analysis are shown in FIG. 3A, which shows clearly that EGF samples appearing pure when analyzed by TFA-based reversed phase HPLC (FIG. 2) actually contain contaminating protein (arrow) that is detectable when analyzed by TEA-based reversed phase HPLC. In particular, the main EGF peak eluted at 15 minutes and at about 30% acetonitrile and, as can be seen in FIG. 3A, was well separated from contaminants not previously revealed when TFA was used as the ion pairing agent. Material eluting in the main absorbance peak was collected and then further analyzed by TEAP-based RP-HPLC using the conditions just described. Results of this analysis are shown in FIG. 3B, which clearly illustrates a single protein species, thus demonstrating the absence of protein contaminants from the EGF sample.

EXAMPLE 2

Analysis of human EGF purity by CE

Figure 4:
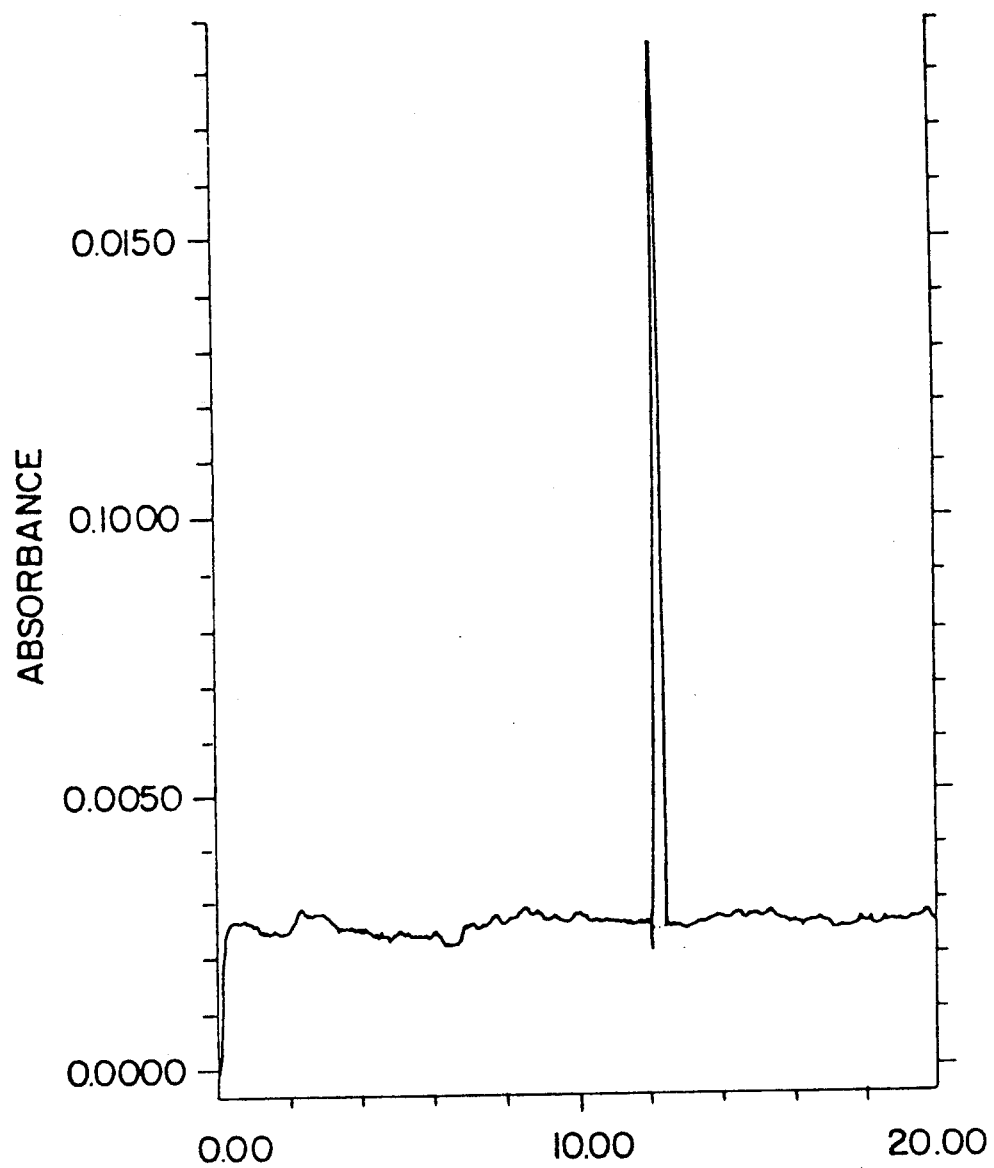
FIG. 4 provides the absorbance ($A_{214}$) profile of the EGF sample shown in FIG. 3B, analyzed by capillary electrophoresis.

Purity of the EGF sample obtained by the TEA-based RP-HPLC method of example 1 was next evaluated using the more sensitive analytical technique of capillary electrophoresis. For this purpose, the capillary electrophoresis device available from Beckman Instruments, Model P/ACE 2000, was used. Samples of EGF recovered from TEA-based HPLC purification (FIG. 3B) and diluted in 150 mM phosphate buffer, pH 2.0-2.3] to yield an EGF concentration in the range between 0.2 mg/ml to 1.0 mg/ml were placed in sample tubes and loaded into the capillary column that had been pre-conditioned with 150 mM phosphate buffer (pH 2.0). Conditions employed to effect separation within the capillary were a voltage of +20 Kv and temperature of 20° C. Sample was loaded by pressure at a rate of about 5 nL/s for from 2-8 seconds, thereby incorporating about 8 nanograms of protein sample into the column. Results of the analysis are shown in FIG. 4, which clearly illustrates the absence of protein contaminants detectable by this ultrasensitive method of protein purity analysis.

We claim:

1. A method for purifying human epidermal growth factor, which comprises the step of fractionating a human epidermal growth factor preparation by reversed phase high performance liquid chromatography in the presence of an amine-based cationic ion-pairing agent or a salt thereof.

2. A method according to claim 1, wherein the amine-based ion-pairing agent is triethylamine.

3. The method according to claim 2, wherein the amine-based cationic ion-pairing agent is triethylamine phosphate.

4. The method according to claim 2 wherein the epidermal growth factor preparation is obtained from a microbial source of human epidermal growth factor.

5. The method according to claim 4, wherein the microbial source of human epidermal growth factor is a bacterial source of human epidermal growth factor.

6. The method according to claim 5 wherein the bacterial source of human epidermal growth factor is an E. coli source of human epidermal growth factor.

7. A method for obtaining essentially pure human epidermal growth factor, comprising the steps of
    i) obtaining a human epidermal growth factor preparation;
    ii) fractionating said preparation by reversed phase high performance liquid chromatography in the presence of triethylamine or a salt thereof; and iii) collecting, following the chromatographic step, essentially pure human epidermal growth factor.

8. The method according to claim 7, comprising the further step of desalting the essentially pure human epidermal growth factor so collected.

9. The method according to claim 8, further comprising the subsequent step of lyophilizing the human epidermal growth factor collected.

10. The method according to claim 7, wherein the epidermal growth factor preparation is obtained from a microorganism.

11. The method according to claim 10, wherein the microorganism is a bacterium.

12. The method according to claim 11, wherein the bacterium is *E. coli*.

* * * * *